(12) United States Patent
Mugford et al.

(10) Patent No.: US 11,441,099 B2
(45) Date of Patent: Sep. 13, 2022

(54) PARTIAL ENZYMATIC HYDROLYSIS OF TRIACYLGLYCEROLS

(71) Applicant: DSM IP Assets B.V., Heerlen (NL)

(72) Inventors: Paul Mugford, Halifax (CA); Monika Mueller, Aachen (DE); Martin Schurmann, Juelich (DE)

(73) Assignee: DSM IP Assets B.V., Heerlen (NL)

( * ) Notice: Subject to any disclaimer, the term of this patent is extended or adjusted under 35 U.S.C. 154(b) by 947 days.

(21) Appl. No.: 16/066,603

(22) PCT Filed: Dec. 29, 2016

(86) PCT No.: PCT/IB2016/058087
§ 371 (c)(1),
(2) Date: Jun. 27, 2018

(87) PCT Pub. No.: WO2017/115323
PCT Pub. Date: Jul. 6, 2017

(65) Prior Publication Data
US 2021/0207060 A1 Jul. 8, 2021

Related U.S. Application Data

(60) Provisional application No. 62/272,833, filed on Dec. 30, 2015.

(51) Int. Cl.
*C12N 9/20* (2006.01)
*C11C 1/04* (2006.01)
*C12P 7/6427* (2022.01)

(52) U.S. Cl.
CPC ............... *C11C 1/045* (2013.01); *C12N 9/20* (2013.01); *C12P 7/6427* (2013.01); *C12Y 301/01003* (2013.01)

(58) Field of Classification Search
CPC ................................ C12N 9/20; C12P 7/6427
See application file for complete search history.

(56) References Cited

FOREIGN PATENT DOCUMENTS

| CN | 1366056 A | 8/2002 |
|---|---|---|
| CN | 104726477 A | 6/2015 |
| EP | 0635574 A1 | 1/1995 |
| EP | 1130100 A1 | 9/2001 |
| WO | WO1993003159 | 2/1993 |
| WO | WO1998046772 | 10/1998 |
| WO | WO1999060102 | 11/1999 |
| WO | WO00/37671 | 6/2000 |
| WO | WO2013043641 A1 | 3/2013 |
| WO | WO2015087833 A1 | 6/2015 |

OTHER PUBLICATIONS

Alexopoulos, C.J., Introductory Mycology, Introductory Mycology, 1952, 482.
Altschul et al., Basic Local Alignment Search Tool, J. Mol. Biol., 1990, 403-410, 215.
Altschul et al., Gapped BLAST and PSI-BLAST: a new generation of protein database search programs, Nucleic Acids Research, 1997, 3389-3402, 25(17).
Arai et al., Cloning and Sequencing of the cDNA encoding lipase I from Trichosporon fermentans WU-C12, FEMS Microbiology Letters, 1997, 183-188, 152.
Ausubel et al, Current Protocols in Molecular Biology Current Protocols in Molecular Biology, Molecular Biiology, Dec. 4, 2003, whole book, Book, John Wiley & Sons, Inc.
Carillo et al., The Multiple Sequence Alignment Problem in Biology, SIAM J. Appl. Math, 1988, 1073-1082, 48(5).
Chang et al., Codon Optimization of Candida rugosa lip 1 Gene for Improving Expression in Pichia pastoris and Biochemical Characterization of the Purified Recombinant LIP1 Lipase, Journal of Agricultural and Food Chemistry, 2006, 815-822, 54(3).
Chang et al., Efficient Production of Active Recombinant Candida rugosa LIP3 Lipase in Pchia pastoris and Biochemical Characterization of the Purified Enzyme, Journal of Agricultural and Food Chemistry, 2006, 5831-5838, 54.
Devereux et al, A comprehensive set of sequence analysis programs for the VAX, Nucleic Acids Research, 1984, 387-395, 12(1).
Fleer et al., Stable Multicopy Vectors for High-Level Secretion of Recombinant Human Serum Albumin by Kluyveromyces Yeasts, Biotechnology, 1991, 968-975, 9, Nature Publishing Group.
Henikoff et al, Amino acid substitution matrices from protein blocks, Biochemistry, 1992, 10915-10919, 89.
J. Sambrook, Molcular Cloning, A Laboratory Manual, 1989, Table of contents, Second.
Needleman et al., A General Method Applicable to the Search for Similarities in the Amino Acid Sequence of Two Proteins, J. Mol. Biol., 1970, 443-453, 48.
Pan et al., Efficient Display of Active *Geotrichum* sp. Lipase on Pichia pastoris Cell Wall and Its Application as a Whole-Cell Biocatalyst to Enrich EPA and DHA in Fish Oil, Journal of Agricultural and Food Chemistry, 2012, 9673-9679, 60.
Russell, Paul R., Transcription of the triose-phosphate-isomerase gene of Schizosaccharomyces pombe initiates from a start point different from that in *Saccharomyces cerevisiae*, Gene, 1985, 125-130, 40.
Shimada et al., cDNA Cloning and Characterization of Geotrichum candidum Lipase II, J. Biochem., 1990, 703-707, 107.

*Primary Examiner* — Tekchand Saidha
(74) *Attorney, Agent, or Firm* — Shannon McGarrah

(57) ABSTRACT

Disclosed herein are host cells transformed with a nucleic acid molecule comprising a polynucleotide sequence, wherein the polynucleotide sequence encodes a polypeptide that hydrolyzes an ester linkage of a triacylglycerol in an oil comprising at least one long-chain polyunsaturated fatty acid, methods for using such host cells, and processes for production of a lipase using such host cells.

22 Claims, No Drawings
Specification includes a Sequence Listing.

SEQUENCE LISTING

```
<160> NUMBER OF SEQ ID NOS: 3

<210> SEQ ID NO 1
<211> LENGTH: 1608
<212> TYPE: DNA
<213> ORGANISM: Candida rugosa

<400> SEQUENCE: 1
atggctccta ccgcaactct tgctaatgga gacactatta ctggcttaaa tgctataatc      60
aacgaggcct ttctgggaat tccattcgca gaacctcctg tcggcaatct acgattcaaa     120
gaccctgtcc catattcagg ttccctcgat ggtcaaaagt tcacttccta cggccctagt     180
tgcatgcagc aaaacccgga aggtacatac gaagagaact taccaaaagc agctttggat     240
ttggttatgc aatccaaagt gttcgaagca gtctcccaa gctcagagga ctgtctaacc      300
atcaatgtcg ttagaccacc cggtacaaaa gctggtgcca atttacctgt aatgctgtgg     360
attttcggtg gaggttttga ggttggggt acatccacat ttcctcccgc acaaatgatc     420
acgaaatcga tcgctatggg taaacctatt atccatgttt cagttaacta ccgtgtatct     480
```

```
tcatggggat ttttggccgg agatgaaatc aaagcagaag gatctgctaa tgctggtttg    540
aaggatcaaa gactcggtat gcagtgggtt gcagacaaca tcgctgcttt cggaggtgac    600
ccaacgaagg tgacaatatt cggtgaatca gctggttcca tgtcggtgat gtgtcacatt    660
ctatggaatg acggtgataa cacatataag ggtaagccac tatttagagc aggaataatg    720
caatccggtg ctatggtgcc atcagatgca gttgacggca tctacggtaa tgagattttc    780
gacttattgg caagcaatgc tggatgtggt tccgcctcgg acaagctggc ttgtctgagg    840
ggagtatctt cggacacctt ggaggatgct actaataaca ctccgggttt cttggcctac    900
tcttctttgc gtcttagtta cttacccaga ccagatggtg tcaacatcac tgatgacatg    960
tatgctctgg tgagagaggg taagtacgcc aatattccag tgatcatcgg agatcagaat   1020
gacgaaggaa ctttctttgg tacttcttca ctgaatgtta ctacagatgc acaggctaga   1080
gagtatttca acagagctt cgtccacgct tctgatgccg agattgatac tcttatgaca   1140
gcttatccag cgacattac acaaggttcc ccttttgata ctggtatttt gaacgctttg   1200
acaccccaat tcaagagaat ctccgctgtt ttgggtgatt tgggttttac cttggcacgt   1260
aggtatttcc ttaatcatta tactggaggg acaaagtata gcttttgtc aaaacaactt    1320 tccggtttgc ctgttttagg aacgtttcat tctaatgata ttgtgtttca agactacctg   1380
ttgggtagcg gtagtttgat atacaacaat gcattcatcg cgtttgcaac tgatttggac   1440
ccaaatacgg ccggtttact ggtaaaatgg ccagaataca catcctcttc ccaaagtgga   1500
aataacctga tgatgattaa tgcactggga ctttacaccg gtaaggacaa ctttagaact   1560
gctggatatg acgctttgtt ttctaaccca cctagttcct tgtttaa              1608
```

<210> SEQ ID NO 2
<211> LENGTH: 1608
<212> TYPE: DNA
<213> ORGANISM: Candida rugosa

<400> SEQUENCE: 2

```
atggctccaa cagctaagtt ggcaaacggt gataccatta ccggtcttaa tgctataatc     60
aatgaagctt tcctgggtat cccttcgcc gaacccccag ttggaaatct ccgtttcaaa    120
gatccagtgc ttattccggg ttcttttgaat ggacagaagt ttacatctta tggtccttca    180
tgtatgcaac aaaatccaga aggaacgttt gaagagaatt gggcaaaaac tgcactggac    240
ttggtcatgc agtcgaaagt ctttcaggcc gtgttaccgc aatccgagga ctgcttgact    300
attaacgtag ttagacctcc aggaactaaa gctggggcta atttgcctgt gatgctgtgg    360
atcttcggtg gtggatttga gatcggttcc ccgactattt tcccacccgc acaaatggtg    420
actaaatcag ttcttatggg taagcctatc attcacgtag ccgttaacta cagggttgcc    480
tcgtggggtt tcttggctgg tgatgacatt aaagctgagg gttccggaaa tgcaggacta    540
aaagatcaac gtttgggtat gcaatgggta gcagacaata ttgccggatt tggaggcgat    600
ccctcaaagg tgacaatttt cggagagagt gctggttcca tgtccgtttt tgtgtcacctg    660 atatggaatg acggtgataa cacatataag ggaaagcctt tgtttcgagc aggcatcatg    720
caatcaggtg caatggtccc atctgaccct gtggatggta catatggcaa tgaaatctat    780 gaccttttg tatctagcgc cggatgtggt tcggcttccg acaagttggc ttgtttgaga    840
tctgcttcca gtgacacttt gcttgatgca actaacaata caccaggatt ctagcatac    900 tcctcattga gactttcata cttgcctaga ccagacggta aaacatcac cgacgacatg    960
```

```
tataagttag ttagagatgg taaatacgct agtgtccctg tcatcatcgg tgatcagaat    1020
gacgagggca ctatctttgg tttaagctct ttaaacgtta cgactaatgc acaagctaga    1080
gcgtacttta agcaatcttt catacatgca tctgatgctg aaatcgatac attgatggcc    1140
gcatacccac aagatattac gcaaggtagc ccatttgaca caggaatttt caatgctatc    1200
acacctcaat tcaaaaggat ttcggctgtc ttgggagatc tggccttcat ccacgctaga    1260
agatatttcc tcaaccattt ccaaggtgga actaagtaca gctttctgag taagcagctt    1320
tccggtttac caattatggg taccttccat gctaatgata tcgtttggca ggactatttg    1380
ctgggttccg gttcagtgat atacaataat gctttcattg catttgcaac agatctggac    1440
cccaacactg ctggtttgct agttaactgg ccaaaataca ctagcagttc acagtccggt    1500
aataacttga tgatgattaa tgcactaggt ctgtacaccg ggaaagataa ctttcgtact    1560
gctggatatg atgctttaat gactaaccca tcttctttct ttgttag              1608

<210> SEQ ID NO 3
<211> LENGTH: 1911
<212> TYPE: DNA
<213> ORGANISM: Geotrichum candidum

<400> SEQUENCE: 3
atgagatttc cttcaatttt tactgctgtt ttattcgcag catcctccgc attagctgct     60
ccagtcaaca ctacaacaga gatgaaacg gcacaaattc cggctgaagc tgtcatcggt    120
tactcagttt agaaggggat ttcgatgttg ctgttttgcc attttccaac agcacaaata    180 acgggtatt gttataaat actactattg ccagcattgc tgctaaagaa gaagggtat     240 ctctcgagaa aagaaggctg aagctcacca tcaccaccat catcaccacc aagctcctac    300
cgcagtcttg aacggtaacg aggtcatttc tggtgtcttg gaaggtaaag tcgacacttt    360
caagggtatc ccttttgctg accaccttg aatgacttga gatttaagca tccacagcca    420
tttactggtt cttaccaagg tttgaaggcc aatgatttct ctccagcctg tatgcagttg    480
gaccctggaa attctttgac cttgttggta aggctttggg attggctaaa gttatcccag    540
aggagtttag aggtcctttg tacgatatgg ctaagggaac tgtctctatg aacgaggatt    600
gcttgtactt gaatgttttt agacctgccg gaactagcca gatgctaagt tgccagttat    660
ggtttggatt tatggtggtg catttgttta cggatcttct gccgcatatc caggtaattc    720
ttacgttaaa gaatctatca acatgggtca acctgttgtt ttgtttctat taactataga    780
acaggacctt tcggttttct gggaggagac gccattactg ccgagggtaa taccaatgct    840
ggattgcacg accagagaaa aggattggaa tgggtttctg ataacattgt aacttcggag    900
gtgaccctga taaagtcatg attttcggtg agtctgctgg tgctatgtct gtcgcccacc    960
agttgattgc ctacggtgga gataacacct ataatggaaa gaagttgttt cattctccat   1020
cttgcagtct ggtggtccat gccataccac gattcttct tctgtcggac cagacatctc   1080
ttataacaga ttcgcccaat atgctggttg tgacacctct gcatctgcaa acgacacatt   1140
ggatgtttga gatctaaatc ttcttctgtt ttgcatgatg cccagaactc ttacgatttg   1200
aaagacttgt tcggattgtt gcctcagttt tgggttttg gaccaagacc agatggtaac   1260
attattcctg tgccgcttac gaattgttca gatctggtag atacgctaag gtcccttata   1320
tctctggaaa ccaagaagac gaaggaactg cttcgctcc agtcgcattg aatgcaacta   1380
ctaccccaca cgttaagagt ggttgcagta tatcttctac gacgcctctg aggcttctat   1440
tgacagagtt ttgtctttgt atcctcagac tttgtctgtt ggttctccat ttagaaccgg   1500
```

-continued

```
tattttgaac gctttgacac cacatttaag agagtcgccg ctatcttgtc tgacatgttg   1560
ttccagtctc ctagaagagt tatgttgtct gccactaagg atgtcaacag atggacctat   1620
ttgtctactc atttgcataa tttggttcca tcttgggtac ttttcatggt aatgaattga   1680
tctttcagtt caacgttaat atcggacctg ctaattctta tttgagatac tttatttctt   1740
tcgccaacca tcacgaccca aacgttggta caaacttgtg caatgggatc aatacacaga   1800
tgaaggaaag gagatgttgg aaatccatat gacagataac gtcatgagaa ccgatgacta   1860
cagaattgaa ggtatctcta atttcgagac cgacgtcaac ttgtaggtta a            1911
```

PARTIAL ENZYMATIC HYDROLYSIS OF TRIACYLGLYCEROLS

CROSS-REFERENCE TO RELATED APPLICATIONS

This application is a National Stage of International Application No. PCT/IB2016/058087 filed Dec. 29, 2016, and which claims the benefit of the filing date of U.S. Provisional Patent Application No. 62/272,833 filed Dec. 30, 2015, 2014, the entire contents of each of which are hereby incorporated herein by reference in their entireties.

FIELD OF THE INVENTION

The present invention relates to host cells transformed with a nucleic acid sequence encoding a lipase gene and methods of using a host cell transformed with a nucleic acid sequence encoding a lipase gene. The lipase gene is expressed in the host cell to confer the ability of hydrolyzing an ester linkage of a triacylglycerol in an oil comprising at least one long-chain polyunsaturated fatty acid. The host cell is used to manufacture sufficient quantities of a lipase so as to be useful for commercial manufacture of oil compositions that are enriched in long-chain polyunsaturated fatty acids. The present invention further relates to nucleic acid sequences encoding lipase genes.

BACKGROUND

Long-chain polyunsaturated fatty acids (LC-PUFAs) such as the omega-3 fatty acids are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits. Indeed, the American Heart Association has also reported that omega-3 fatty acids can reduce cardiovascular and heart disease risk. Other benefits of LC-PUFAs are those related to the prevention and/or treatment of inflammation, neurodegenerative diseases, and cognitive development. Diets rich in LC-PUFAs like omega-3 fatty acids have also been shown to have beneficial effects for heart disease, cancer, arthritis, allergies, and other chronic diseases.

LC-PUFAs, such as, for example, omega-3 fatty acids, are often derived from marine oils, microbial, and/or algal oils. Such sources typically contain LC-PUFAs in a triacylglycerol form where other undesired fatty acids (e.g., saturated fatty acids) are present alongside a desired LC-PUFA(s) in the triacylglycerol molecule. Thus, purifying and concentrating LC-PUFAs in oils is generally desired.

Various methods of producing LC-PUFA concentrates from oils, such as marine, microbial, and/or algal oils, are known. For example, lipases have been used to transesterify saturated fatty acids from triacylglycerols into ethyl esters. The saturated fatty acids are then removed from the mixture by distillation, and the unsaturated esters are sometimes transesterified back to triacylglycerols. Other methods selectively hydrolyze saturated fatty acids from triacylglycerols with lipases and the resulting free saturated fatty acids are removed by forming a complex with urea. The amount of LC-PUFAs contained in oils obtained by these methods is generally 60 wt. % or higher, or 70 wt. % or higher relative to the amount of the fatty acids.

It has been found that current commercial lipases have varying degrees of effectiveness when used in hydrolyzation reactions, particularly when used in crude and refined fish oil. Improving the selectivity and reaction rate of the lipases would give a higher yield of oil and more efficient processing. For example, some lipases will indiscriminately hydrolyze all available fatty acids from the glyceride. Others will show undesired selectivity towards which fatty acids are hydrolyzed from the glyceride. It would be advantageous to leave the desired LC-PUFAs such as EPA and DHA on the glyceride to more efficiently and effectively enable the concentration of these LC-PUFAs in later downstream processing steps. Identification and isolation of lipases that would allow for such selectivity and/or improved reaction rate would, therefore, be very useful. The inventors have identified isoforms of lipases that are more selective for the desired LC-PUFAs such as EPA and DHA, and have a higher reaction rate.

SUMMARY OF THE INVENTION

Disclosed herein are host cells transformed with a nucleic acid molecule comprising a polynucleotide sequence, wherein the polynucleotide sequence encodes a polypeptide that hydrolyzes an ester linkage of a triacylglycerol in an oil, methods for using such host cells, and processes for production of a lipase using such host cells.

In some embodiments, the polynucleotide sequence has at least 75% identity to SEQ ID NO: 1. In a preferred embodiment, the polynucleotide sequence has at least 80% identity to SEQ ID NO: 1. In a more preferred embodiment, the polynucleotide sequence has at least 90% identity to SEQ ID NO:1. In some embodiments, the polynucleotide sequence has at least 75% identity to SEQ ID NO:2. In a preferred embodiment, the polynucleotide sequence has at least 80% identity to SEQ ID NO: 2. In a more preferred embodiment, the polynucleotide sequence has at least 90% identity to SEQ ID NO:2. In some embodiments, the polynucleotide sequence has at least 75% identity to SEQ ID NO:3. In a preferred embodiment, the polynucleotide sequence has at least 80% identity to SEQ ID NO: 3. In a more preferred embodiment, the polynucleotide sequence has at least 90% identity to SEQ ID NO:3.

In some embodiments, the polynucleotide sequence encodes a lipase gene. In a preferred embodiment, the polynucleotide sequence encodes an isoform of a lipase gene. In a more preferred embodiment, the polynucleotide sequence encodes an isoform of a *Candida rugosa* or a *Geotrichum candidum* lipase gene.

In some embodiments, the host cell is a yeast. In a preferred embodiment, the host cell is *Pichia pastoris*.

In some embodiments, the triacylglycerol comprises at least one long-chain polyunsaturated fatty acid (LC-PUFA). In some embodiments, the LC-PUFA comprises docosahexaenoic acid (DHA), eicosapentaenoic acid (EPA), and mixtures thereof. In another embodiment, the LC-PUFA is DHA. In a further embodiment, the LC-PUFA is EPA.

DESCRIPTION OF THE INVENTION

The nucleic acid sequences and deduced amino acid translation sequences listed in the accompanying sequence listing are shown using standard letter abbreviations for nucleotide bases and amino acids, as defined in 37 C.F.R § 1.822. In the case of DNA sequences, only one strand of each nucleic acid sequence is shown, but the complementary strand is understood to be included by any reference to the displayed strand. In the accompanying sequence listing:

SEQ ID NO:1 shows the nucleotide sequence encoding the *Candida rugosa* isoform lipase 1 (CR Lip1) DNA sequences, codon optimized for expression in *Pichia pastoris*:

```
atggctcctaccgcaactcttgctaatggagacactattactggcttaa
atgctataatcaacgaggcctttctgggaattccattcgcagaacctcc
tgtcggcaatctacgattcaaagaccctgtcccatattcaggttccctc
gatggtcaaaagttcacttcctacggccctagttgcatgcagcaaaacc
cggaaggtacatacgaagagaacttaccaaaagcagctttggatttggt
tatgcaatccaaagtgttcgaagcagtctccccaagctcagaggactgt
ctaaccatcaatgtcgttagaccacccggtacaaaagctggtgccaatt
tacctgtaatgctgtggattttcggtggaggttttgaggttggggtac
atccacatttcctcccgcacaaatgatcacgaaatcgatcgctatggt
aaacctattatccatgtttcagttaactaccgtgtatcttcatgggat
ttttggccgagatgaaatcaaagcagaaggatctgctaatgctggttt
gaaggatcaaagactcggtatgcagtgggttgcagacaacatcgctgct
ttcggaggtgacccaacgaaggtgacaatattcggtgaatcagctggtt
ccatgtcggtgatgtgtcacattctatggaatgacggtgataacacata
taagggtaagccactatttagagcaggaataatgcaatccggtgctatg
gtgccatcagatgcagttgacggcatctacggtaatgagattttcgact
tattggcaagcaatgctggatgtggttccgcctcggacaagctggcttg
tctgagggagtatcttcggacaccttggaggatgctactaataacact
ccgggtttcttggcctactcttctttgcgtcttagttacttaccagac
cagatggtgtcaacatcactgatgacatgtatgctctggtgagagaggg
taagtacgccaatattccagtgatcatcggagatcagaatgacgaagga
actttctttggtacttcttcactgaatgttactacagatgcacaggcta
gagagtatttcaaacagagcttcgtccacgcttctgatgccgagattga
tactcttatgacagcttatccaggcgacattacacaaggttcccctttt
gatactggtatttttgaacgctttgacaccccaattcaagagaatctccg
ctgttttgggtgatttgggttttaccttggcacgtaggtatttccttaa
tcattatactggagggacaaagtatagcttttttgtcaaaacaactttcc
ggtttgcctgttttaggaacgtttcattctaatgatattgtgtttcaag
actacctgttgggtagcggtagtttgatatacaacaatgcattcatcgc
gtttgcaactgatttggacccaaatacggccggtttactggtaaaatgg
ccagaatacacatcctcttcccaaagtggaaataacctgatgatgatta
atgcactgggactttacaccggtaaggacaactttagaactgctggata
tgacgctttgttttctaacccacctagtttctttgtttaa
```

SEQ ID NO:2 shows the nucleotide sequence encoding the *Candida rugosa* isoform lipase 3 (CR Lip3) DNA sequences, codon optimized for expression in *Pichia pastoris*:

```
atggctccaacagctaagttggcaaacggtgataccattaccggtctta
atgctataatcaatgaagctttcctgggtatcccttccgccgaaccccc
agttggaaatctccgtttcaaagatccagtgccttattccggttctttg
aatggacagaagtttacatcttatggtccttcatgtatgcaacaaaatc
cagaaggaacgtttgaagagaatttgggcaaaactgcactggacttggt
catgcagtcgaaagtctttcaggccgtgttaccgcaatccgaggactgc
ttgactattaacgtagttagacctccaggaactaaagctggggctaatt
tgcctgtgatgctgtggatcttcggtggtggatttgagatcggttcccc
gactattttcccacccgcacaaatggtgactaaatcagttcttatgggt
aagcctatcattcacgtagccgttaactacagggttgcctcgtggggtt
tcttggctggtgatgacattaaagctgagggttccggaaatgcaggact
aaaagatcaacgtttgggtatgcaatgggtagcagacaatattgccgga
tttggaggcgatccctcaaaggtgacaattttcggagagagtgctggtt
ccatgtccgttttgtgtcacctgatatggaatgacggtgataacacata
taagggaaagcctttgtttcgagcaggcatcatgcaatcaggtgcaatg
gtcccatctgaccctgtggatggtacatatggcaatgaaatctatgacc
ttttgtatctagcgccggatgtggttcggcttccgacaagttggcttg
tttgagatctgcttccagtgacactttgcttgatgcaactaacaataca
ccaggatttctagcatactcctcattgagactttcatacttgcctagac
cagacggtaaaaacatcaccgacgacatgtataacttagttagagatgg
taaatacgctagtgtccctgtcatcatcggtgatcagaatgacgagggc
actatctttggtttaagctcttaaacgttacgactaatgcacaagcta
gagcgtacttaagcaatcttcatacatgcatctgatgctgaaatcga
tacattgatggccgcatcccacaagatattacgcaaggtagcccattt
gacacaggaattttcaatgctatcacacctcaattcaaaaggatttcgg
ctgtcttgggagatctggccttcatccacgctagaagatatttcctcaa
ccatttccaaggtggaactaagtacagctttctgagtaagcagctttcc
ggtttaccaattatgggtaccttccatgctaatgatatcgtttggcagg
actatttgctgggttccggttcagtgatataacaataatgctttcattgc
atttgcaacagatctggacccaacactgctggtttgctagttaactgg
ccaaaatacactagcagttcacagtccggtaataacttgatgatgatta
atgcactaggtctgtacaccgggaaagataactttcgtactgctggata
tgatgctttaatgactaacccatcttctttctttgtttag
```

SEQ ID NO:3 shows the nucleotide sequence encoding the *Geotrichum candidum* isoform lipase 2 (GC Lip2) DNA sequences:

```
atgagatttccttcaattttttactgctgttttattcgcagcatcctccg
cattagctgctccagtcaacactacaacagaagatgaaacggcacaaat
tccggctgaagctgtcatcggttactcagtttagaaggggatttcgatg
ttgctgttttgccattttccaacagcacaaataacgggttattgtttat
aaatactactattgccagcattgctgctaaagaagaaggggtatctctc
```

-continued

```
gagaaaagaaggctgaagctcaccatcaccaccatcatcaccaccaagc
tcctaccgcagtcttgaacggtaacgaggtcatttctggtgtcttggaa
ggtaaagtcgacactttcaagggtatccttttgctgaccacctttgaa
tgacttgagatttaagcatccacagccatttactggttcttaccaaggt
ttgaaggccaatgatttctctccagcctgtatgcagttggaccctggaa
attctttgaccttgttggtaaggctttgggattggctaaagttatccca
gaggagtttagaggtcctttgtacgatatggctaagggaactgtctcta
tgaacgaggattgcttgtacttgaatgttttagacctgccggaactag
ccagatgctaagttgccagttatggtttggatttatggtggtgcatttg
tttacggatcttctgccgcatatccaggtaattcttacgttaaagaatc
tatcaacatgggtcaacctgttgttttgtttctattaactatagaacag
gacctttcggttcttgggaggagacgccattactgccgagggtaatac
caatgctggattgcacgaccagagaaaggattggaatgggtttctgat
aacattgtaacttcggaggtgaccctgataaagtcatgattttcggtga
gtctgctggtgctatgtctgtcgccaccagttgattgcctacggtgga
gataacacctataatggaaagaagttgtttcattctccatcttgcagtc
tggtggtccattgccataccacgattcttcttctgtcggaccagacatc
tcttataacagattcgcccaatatgctggttgtgacacctctgcatctg
caaacgacacattggatgtttgagatctaaatcttcttctgttttgcat
gatgccagaactcttacgatttgaaagacttgttcggattgttgcctc
agttttgggttttggaccaagaccagatggtaacattattcctgtgcc
gcttacgaattgttcagatctggtagatacgctaaggtcccttatatct
ctggaaaccaagaagacgaaggaactgctttcgctccagtcgcattgaa
tgcaactactacccacacgttaagagtggttgcagtatatcttctacg
acgcctctgaggcttctattgacagagttttgtctttgtatcctcagac
tttgtctgttggttctccatttagaaccggtattttgaacgctttgaca
ccacatttaagagagtcgccgctatcttgtctgacatgttgttccagtc
tcctagaagagttatgttgtctgccactaaggatgtcaacagatggacc
tatttgtctactcatttgcataatttggttccatcttgggtacttttca
tggtaatgaattgatctttcagttcaacgttaatatcggacctgctaat
tcttatttgagatactttatttctttcgccaaccatcacgacccaaacg
ttggtacaaacttgtgcaatgggatcaatacacagatgaaggaaaggag
atgttggaaatccatatgacagataacgtcatgagaaccgatgactaca
gaattgaaggtatctctaatttcgagaccgacgtcaacttgtaggttaa
```

DETAILED DESCRIPTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined so as to sub-combinations thereof.

Embodiments identified herein as exemplary are intended to be illustrative and not limiting.

In this specification and in the claims that follow, reference will be made to a number of terms, which shall be defined to have the following meanings:

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

"Optional" or "optionally" means that the subsequently described event or circumstance can or cannot occur, and that the description includes instances where the event or circumstance occurs and instances where it does not.

The term "triacylglycerol" or "TAG" is used to refer to a molecule comprising a glycerol ester of a fatty acid. This term is also used synonymously with "triglyceride" (TG). "Glyceride" is used to refer to mono-, di- and/or triglycerides, as the context dictates.

Polyunsaturated fatty acids (PUFAs) are classified based on the position of the first double bond from the methyl end of the fatty acid; omega-3 (n-3) fatty acids contain a first double bond at the third carbon, while omega-6 (n-6) fatty acids contain a first double bond at the sixth carbon. For example, docosahexaenoic acid (DHA) is an omega-3 long-chain polyunsaturated fatty acid (LC-PUFA) with a chain length of 22 carbons and 6 double bonds, often designated as "22:6n-3." A long-chain polyunsaturated fatty acid (LC-PUFA) has a number of carbon atoms from 20 to 24 and the number of unsaturations is 4 or 5. PUFAs and LC-PUFAs can be in free form, ester, or glyceride form.

Sequence Identity and Similarity

Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, N.J., 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g., the GCG program package (Devereux, J., et al., Nucleic Acids Research 12 (1):387 (1984)), BestFit, BLASTP, BLASTN, and FASTA (Altschul, S. F. et al., J. Mol. Biol. 215:403-410 (1990)). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990)). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Disclosed herein are host cells transformed with a nucleic acid molecule comprising a polynucleotide sequence, wherein the polynucleotide sequence encodes a polypeptide that hydrolyzes an ester linkage of a triacylglycerol in an oil comprising at least one long-chain polyunsaturated fatty acid, methods for using such host cells, and processes for production of a lipase gene using such host cells.

In one embodiment, the host cell has the ability of producing triglyceride-hydrolyzing lipases in high yield. The ability to produce these lipases is conferred to the host cell by transformation of the host cell with a nucleic acid construct comprising a polynucleotide sequence encoding a lipase gene. The transformed host cell's ability to produce these lipases is a combination of the transvection of the lipase-encoded sequence from expression hosts such as *Candida rugosa* or *Geotrichum candidum*, and promoter genes such as AOX or GAP. The lipase genes are fused to the alpha mating factor of *Saccharomyces cerevisiae* enabling the secretion of recombinant lipases to the culture supernatant. The alpha mating factor is cleaved upon export of the native protein. This also allows the lipase to be harvested without destruction of the host cell.

The nucleotide sequence encodes a lipase gene that is preferably expressed in excretable form in the transformed host cell and is then excreted in active form out of the host cell. Thus, expression of the nucleotide sequence in the host cell produces a lipase which, when transported out of the host cell, has an expression level of greater than 1 U/mL cell culture, preferably at least 2, 3, 4, 5, 10, 20, 40, 60, or 80 U/mL at 28° C. One unit of activity (U) is defined as the amount of enzyme that produced 1 µmol p-nitrophenol per minute under standard conditions (100 mM MOPS buffer pH 7.5, 0.24 mM p-nitrophenyl ester, 37° C.). Determination of the lipase activity, amount of cell culture, and preparation of the cell free lipase were measured by spectrophotometric activity assay as described in the corresponding test method section, with para-nitrophenyl butyrate (p-NPD) as substrate.

A host cell for transformation with a polynucleotide sequence encoding a polypeptide that hydrolyzes an ester linkage of a triacylglycerol is preferably a host capable of aerobic fermentation. The host cell further preferably has a high tolerance to ethanol and organic acids like lactic acid, acetic acid or formic acid and sugar degradation products such as furfural and hydroxy-methylfurfural. Any of these characteristics or activities of the host cell may be naturally present in the host cell or may be introduced or modified by genetic modification. A suitable host cell is a microorganism like a bacterium or a fungus, however, most suitable as host cell are yeasts or filamentous fungi. Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form. Yeasts may either grow by budding of a unicellular thallus or may grow by fission of the organism. Preferred yeasts as host cells belong to the genera *Saccharomyces, Kluyveromyces, Candida, Pichia, Schizosaccharomyces, Hansenula, Kloeckera, Schwanniomyces*, Geotrichia, and *Yarrowia*.

In a preferred embodiment, the nucleic acid construct confers to the host cell the ability to generate polypeptides, such as lipase enzymes, and emit them from the cell. The transformed host cell has the ability to grow in various media designed for yeast cultivation. The transformed host cell of the invention thus extracellularly expresses a lipase at a specific activity level dependent on plasmid design and cultivation conditions.

Transformation of host cells with the nucleic acid constructs of the invention and additional genetic modification of host cells, preferably yeasts, as described above, may be carried out by methods well known in the art. Such methods are e.g., known from standard handbooks, such as Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g., EP-A-0 635 574, WO 98/46772, WO 99/60102 and WO 00/37671.

In some embodiments, the nucleic acid construct comprises a polynucleotide sequence encoding a lipase gene and used for transformation of a host cell. In the nucleic acid construct, the polynucleotide sequence encoding the lipase gene preferably is operably linked to a promoter for control and initiation of transcription of the polynucleotide sequence in a host cell. The promoter preferably is capable of causing sufficient expression of the lipase in the host cell to confer to the host cell the ability to generate the lipase and excrete it from the cell. Preferably, the promoter maximizes the lipase production in the host cell. Promoters useful in the nucleic acid constructs of the invention include both constitutive and inducible natural promoters as well as engineered promoters. Promotors having these characteristics are widely available and known to the skilled person. Suitable examples of such promoters include e.g., yeast promoters from glycolytic genes, such as the yeast phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK) promoters, TEF1-alpha gene promoters, PHO90, TH11, and AOD promoters; more details about such promoters may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Most preferred are the promoters from the *Pichia* expression vector pD912 (strong methanol inducible AOX promoter) and *Pichia* expression vector pD915 (medium strong constitutive GAP promoter). Other promoters, both constitutive and inducible, and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the lipase is homologous to the host cell in which the lipase isomerase is expressed.

In the nucleic acid construct, the 3'-end of the nucleotide acid sequence encoding the lipase gene preferably is operably linked to a polynucleotide encoding a secretion factor sequence that enables the secretion of recombinant lipases to the culture supernatant and is subsequently cleaved upon export of the lipase. Preferably, the secretion factor sequence is operable in a host cell of choice, such as e.g., the yeast species of choice. In any case the choice of the factor is not critical, it may e.g., be from any yeast gene, although secretion factors may sometimes work if from a non-yeast, eukaryotic, gene. The secretion factor sequence further preferably comprises an alpha mating factor of *Saccharomyces cerevisae*.

Optionally, a selectable marker may be present in the nucleic acid construct. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g., dihydrofolate reductase, hygromycin-B-phosphotransferase, zeocin, 3'-O-phosphotransferase II (kanamycin, neomycin and G418 resistance). Although the use of antibiotic resistance markers may be most convenient for the transformation of polyploid host cells, preferably however, non-antibiotic resistance markers are used, such as auxotrophic markers (URA3, TRP1, LEU2) or the *S. pombe* TPI gene (described by Russell P R, 1985, Gene 40: 125-130). The host cells transformed with the nucleic acid constructs can be marker-gene free. Methods for constructing recombinant marker-gene free microbial host cells are disclosed in EP-A-0 635 574 and are based on the use of bidirectional markers such as the *A. nidulans* amdS (acetamidase) gene or the yeast URA3 and LYS2 genes. Alternatively, a screenable marker such as Green Fluorescent Protein, lacZ, luciferase, chloramphenicol acetyltransferase, beta-glucuronidase may be incorporated into the nucleic acid constructs of the invention allowing to screen for transformed cells.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g., be based on the yeast 2.mu. or pKD1 (Fleer et al., 1991, Biotechnology 9:968-975) plasmids. Alternatively, the nucleic acid construct may comprise sequences for integration, preferably by homologous recombination. Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In one embodiment, the present invention relates to a host cell transformed with a nucleic acid comprising a polynucleotide sequence, wherein the polynucleotide sequence encodes a polypeptide that hydrolyzes an ester linkage of a triacylglycerol in an oil comprising at least one long-chain polyunsaturated fatty acid.

In another embodiment, the present invention relates to a method of using a host cell transformed with a nucleic acid molecule comprising a polynucleotide sequence, wherein the polynucleotide sequence encodes a polypeptide that hydrolyzes an ester linkage of a triacylglycerol in an oil comprising at least one long-chain polyunsaturated fatty acid.

In some embodiments, the host cell is transformed with a nucleic acid molecule comprising a polynucleotide sequence having at least 60, 65, 70, 75, 80, 85, 90, 91, 92, 93, 94, 95, 96, 97, 98, 99% identity to SEQ ID NO: 1. In some embodiments, the host cell is transformed with a nucleic acid molecule comprising a polynucleotide sequence having a 60% to 99%, a 65% to 99%, a 70% to 99%, a 75% to 99%, a 80% to 99%, a 85% to 99%, a 90% to 99%, a 91% to 99%, a 92% to 99%, a 93% to 99%, a 94% to 99%, a 95% to 99%, a 96% to 99%, a 97% to 99%, or a 98% to 99% identity to SEQ ID NO:1.

In another embodiment, the host cell is transformed with a nucleic acid molecule comprising a polynucleotide sequence having at least 65, 70, 75, 80, 85, 90, 91, 92, 93, 94, 95, 96, 97, 98, 99% identity to SEQ ID NO: 2. In some embodiments, the host cell is transformed with a nucleic acid molecule comprising a polynucleotide sequence having a 60% to 99%, a 65% to 99%, a 70% to 99%, a 75% to 99%, a 80% to 99%, a 85% to 99%, a 90% to 99%, a 91% to 99%, a 92% to 99%, a 93% to 99%, a 94% to 99%, a 95% to 99%, a 96% to 99%, a 97% to 99%, or a 98% to 99% identity to SEQ ID NO:2.

In another embodiment, the host cell is transformed with a nucleic acid molecule comprising a polynucleotide sequence having at least 65, 70, 75, 80, 85, 90, 91, 92, 93, 94, 95, 96, 97, 98, 99% identity to SEQ ID NO: 3. In some embodiments, the host cell is transformed with a nucleic acid molecule comprising a polynucleotide sequence having a 60% to 99%, a 65% to 99%, a 70% to 99%, a 75% to 99%, a 80% to 99%, a 85% to 99%, a 90% to 99%, a 91% to 99%, a 92% to 99%, a 93% to 99%, a 94% to 99%, a 95% to 99%, a 96% to 99%, a 97% to 99%, or a 98% to 99% identity to SEQ ID NO:3.

In some embodiments, the polynucleotide sequence encodes a lipase gene. In a preferred embodiment, the polynucleotide sequence encodes an isoform of a lipase gene. In a more preferred embodiment, the polynucleotide sequence encodes an isoform of a lipase derived from *Candida rugosa* or a *Geotrichum candidum* lipase gene.

In some embodiments, the polypeptide that hydrolyzes an ester linkage of a triacylglycerol in an oil is a lipase. In a preferred embodiment, the polypeptide that hydrolyzes an ester linkage of a triacylglycerol in an oil is an isoform of a lipase. In a more preferred embodiment, the polypeptide that hydrolyzes an ester linkage of a triacylglycerol in an oil is an isoform of a lipase derived from *Candida rugosa* or *Geotrichum candidum*.

In some embodiments, the host cell is a yeast. In a preferred embodiment, the host cell is *Pichia pastoris*.

In one embodiment, the lipase is a mixture of isoforms derived from *Candida rugosa*. In a preferred embodiment, the lipase is an isoform derived from *Candida rugosa*. In a more preferred embodiment, the lipase is *Candida rugosa* lipase 1, *Candida rugosa* lipase 3, and mixtures thereof.

In one embodiment, the lipase is a mixture of isoforms derived from *Geotrichum candidum*. In a preferred embodiment, the lipase is an isoform derived from *Geotrichum candidum*. In a more preferred embodiment, the lipase is *Geotrichum candidum* lipase 2.

In some embodiments, the triacylglycerol comprises at least one long-chain polyunsaturated fatty acid (LC-PUFA). In some embodiments, the LC-PUFA comprises an omega-3 fatty acid, an omega-6 fatty acid, and mixtures thereof. In a preferred embodiment, the LC-PUFA comprises docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof. In a more preferred embodiment, the LC-PUFA comprises DHA, EPA, and mixtures thereof. In a further embodiment, the LC-PUFA is DHA. In yet a further embodiment, the LC-PUFA is EPA.

In some embodiments, the host cells are yeasts. Preferably the yeast is capable of aerobic fermentation. In one embodiment, the host cell is *Pichia pastoris*. In another embodiment, the host cell is *Escherichia coli*.

In some embodiments, the oil can be derived from marine oils, such as fish oil. Such oils typically contain mixtures of saturated and unsaturated fatty acids, esters, and glycerides thereof, but can be processed to result in a particular mixture of fatty acids (e.g., containing all saturated, all unsaturated, mixtures of both, or mixtures with fatty acids of a certain chain length or range of chain lengths). Any fish oil can be used in the disclosed compounds and methods. Examples of suitable fish oils include, but are not limited to, Atlantic fish oil, Pacific fish oil, Mediterranean fish oil, light pressed fish oil, alkali treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, herring oil, mackerel oil, salmon oil, and shark oil, including mixtures and combinations thereof. Non-alkali treated fish oil is also suitable. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed compositions and in the disclosed methods to prepare them. Further oils include, a microbial oil that is an algal oil (e.g., oil from a dinoflagellate such as *Crypthecodinium cohnii, Phythium*) or a microbial oil that is a fungal oil (e.g., oil from *Thraustochytrium, Schizochytrium, Mortierella alpina*, or a mixture thereof), and/or plant oil, including mixtures and combinations thereof. In a preferred embodiment, the oil is a crude or unrefined oil.

In one embodiment, the process for the production of a lipase comprises the steps of: a) fermenting a medium containing a host cell transformed to generate and excrete a lipase, as defined herein, whereby the host cell ferments and, concomitantly generates and excretes the lipase; and optionally, b) recovery of the lipase. The fermentation process is preferably run at a temperature that is optimal for the transformed host cell. Thus, for most yeasts or fungal host cells, the fermentation process is performed at a temperature which is less than 38° C. For yeast or filamentous fungal host cells, the fermentation process is preferably performed at a temperature which is lower than 35, 33, 30 or 28° C. and at a temperature which is higher than 20, 22, or 25° C. The fermentation medium may be further optimized to enhance these process steps by any variety of medium compositions known to those skilled in the art. In a preferred embodiment, the lipase is selected from the group consisting of *Candida rugosa* lipase 1, *Candida rugosa* lipase 3, and *Geotrichum candida* lipase 2.

EXAMPLES

Test Methods

Spectrophotometric activity assay: To determine the activity of the lipases, a spectrophotometric assay at 37° C. was used in which p-nitrophenylesters are hydrolyzed. The increase of absorbance at 410 nm caused by the formed p-nitrophenol could be measured and correlates with the enzyme activity. One unit of activity (U) was defined as the amount of enzyme that produced 1 μmol p-nitrophenol per minute under the used conditions. Therefore, a reaction mixture containing 100 mM MOPS buffer pH 7.5, 0.24 mM p-nitrophenylester and 38 μl/ml CFE in a suitable dilution was used as well as blanks containing buffer instead of CFE and the absorbance change was recorded for 5 min. Based on this Δabs/min the volumetric activity (U/ml, see equation 1) and the protein specific activity (U/mg total protein, see equation 2) could be calculated. Measured were the CFE containing the soluble protein fraction (Soluble) and the CFE containing the total protein (Total). In first instance, p-nitrophenylbutyrat (pNPB) was used as substrate.

$$\frac{U}{ml} = \left(\left(\frac{\Delta abs_{CFE}}{min} - \frac{\Delta abs_{blank}}{min}\right) * Df * 26\right) / (\varepsilon * d) \quad (1)$$

with: $Df$ = dilution factor of the CFE $\varepsilon = 12.643 \; (\mu mol/ml)^{-1} * cm^{-1}$ $d$ = path length cuvette $$\frac{U}{mg} = \text{volumetric activity } \frac{U}{ml} / \text{protein concentration } \frac{mg}{ml} \quad (2)$$

Determination of free fatty acids: To determine the percentage of free fatty acids (% FFA) an endpoint titration with Titrino 718 was used. 50 ml of a solvent (toluene/isopropanol/water=500/500/10) was mixed with two drops of phenolphthalein (0.8% (w/w) in isopropanol) and titrated with 0.15 M KOH (10.0 g KOH dissolved in 50 ml water and filled up with 950 ml Ethanol) till color of the solutions stayed pink for 10-15 seconds. To determine the titer, a known amount of benzoic acid was added to the solution and titrated. The titer was calculated as described in equation 3 and for further calculation, the mean of three independent titer-determinations was used. For measuring samples, a known amount of the oil layer of the sample was added to the pink solvent, mixed well and the titrated back to pink. The percentage of FFA was calculated as described in equation 4.

$$\text{titer=m/Mw(Ba)/V(KOH)} \quad (3)$$

with: titer in mol/l
m=mass of used benzoic acid in g
Mw(Ba)=molecular weight of benzoic acid (122.12 g/mol)
V(KOH)=volume of used 0.15 M KOH in l $$\%FFA=V(KOH)*titer*Mw(KOH)/m \quad (4)$$

with: titer in mol/l
m=mass of used sample in g
Mw(KOH)=molecular weight of KOH (56.1 g/mol)
V(KOH)=volume of used 0.15 M KOH in l Determination of EPA and DHA concentration in oil phase (on glycerol) by LC-MS: For the analysis of EPA and DHA concentration, approximately 40 mg of the oil layer were dissolved in 25 ml tetrahydrofuran and further diluted 1:4. The samples were analyzed by LC-MS per typical protocols for such instruments. Column used was a Waters Acquity UPLC BEH C18 50×2.1 mm ID 1.8 µm with pre-column VanGuard. The system was calibrated for DHA and EPA. Calibration curves were generated for both compounds. The results showed that EPA and DHA were well separated thus allowing for accurate calculations of free fatty acids for each.

Example 1—Expression of Candida rugosa Lipase Isoforms in Pichia pastoris

The isoforms in two commercially available Candida rugosa lipases, Amano AY and BioCataysts Lipomod 034, were measured by protein-MS sequencing. 5 CR isoforms were found and the two major isoforms identified in both lipases were CR Lip1 and CR Lip3. Genes for all 5 isoforms were prepared and codon-optimized for expression in Pichia pastoris by DNA2.0 (Menlo Park, Calif.). Lipase genes were fused to the alpha mating factor gene of Saccharomyces cerevisiae enabling the secretion of recombinant lipases to the culture supernatant. The alpha mating factor was cleaved upon export of the native protein. Two expression vectors were prepared, one having an AOX promoter (pD912) and the other having a GAP promoter (pD915), and each individually cloned into Pichia pastoris. In pD912, the gene of interest is cloned downstream and in fusion with the alpha-factor and is under control of the strong methanol inducible AOX promoter. In pD915, the gene of interest is cloned downstream and in fusion with the alphafactor and is under control of the medium strong constitutive GAP promoter. For both pD912 and pD915, zeocin was the selection marker and upon integration into the Pichia genome, pUC origin necessary for propagation in E. coli was removed. 10 of the DNA constructs were prepared by DNA2.0 (Menlo Park, Calif.) and used in each of 2 vectors prepared by DNA2.0. A positive control was also used (pJ912_cutinase from DNA2.0).

Transformation of E. coli with the Pichia Expression Vectors pD912 and pD915 Containing Candida rugosa Lipase Isoform Genes For transformation of P. pastoris, a high amount of plasmid DNA is needed. The DNA prepared by DNA2.0 was propagated in E. coli. Competent cells were generated. The resulting stock was converted to a glycerol stock and the remaining culture was used to extract plasmid DNA.

Extraction of Plasmid-DNA from E. coli

Extraction of plasmid-DNA from the remaining culture was achieved by using the standard protocol from Qiagen ("plasmid DNA purification using Qiagen Plasmid Midi Kit"). The obtained plasmid DNA was analyzed on 0.8% agarose Gel and DNA concentration was measured. The results are shown in Table 1.

TABLE 1

DNA Concentration in Midiprep Samples

| Sample ID | DNA concentration (ng/µl) |
|---|---|
| 912-1 | 685.9 |
| 912-2 | 553.2 |
| 912-3 | 749.6 |
| 912-4 | 683.5 |
| 912-5 | 825.5 |
| 915-1 | 700.5 |
| 915-2 | 409.9 |
| 915-3 | 613.5 |
| 915-4 | 670.2 |
| 915-5 | 793.5 |
| cutinase | 578.2 |

Transformation of Pichia pastoris PPS9010 with pD912 and pD915 Containing Candida rugosa Lipase Isoform Genes Plasmid linearization: The plasmids, which were propagated and therefore available in higher amount, had to be linearized (linear DNA is necessary for transformation of Pichia pastoris). For linearization the following restrictions enzymes were used: For pD912-constructs SacI was used (incubation-temperature 37° C.) and for pD915-constructs SwaI was used (incubation-temperature 25° C.).

To 20 µg DNA (obtained from the Midiprep), 10 µl 10×buffer and 2.5 µl of the restriction-enzyme was added. The mixture was filled up to 100 µl with water. The incubation was run at the appropriate temperature for the restriction enzyme for two hours. The enzymes were then deactivated by exposing the mixture to 65° C. for 20 min. 1 µl mixture was analyzed on 0.8% agarose-gel to verify that the restriction was successful. The achieved linearized DNA was purified using Quiagen PCR Purification Kit by following the supplier's manual. After purification, DNA concentration was measured. The results are shown in Table 2.

TABLE 2

DNA Concentration in purified, linearized plasmid DNA

| Sample ID | DNA concentration (ng/µl) |
|---|---|
| 912-1 | 685.9 |
| 912-2 | 553.2 |
| 912-3 | 749.6 |
| 912-4 | 683.5 |
| 912-5 | 825.5 |
| 915-1 | 700.5 |
| 915-2 | 409.9 |
| 915-3 | 613.5 |
| 915-4 | 670.2 |
| 915-5 | 793.5 |
| cutinase | 578.2 |

Preparation of Competent *Pichia pastoris* Cells 5 ml YPD medium was inoculated with *Pichia pastoris* PPS9010 cells from the glycerol stock using an inoculation loop and was incubated overnight at 30° C. and 180 rpm. This culture was used to inoculate 100 ml fresh YPD medium to an $OD_{600}$ of 0.15-0.2 and this was then incubated at 30° C. and 120 rpm. When $OD_{600}$ reached 1.3-1.5, the culture was filled into two 50 ml Falcon tubes and centrifuged at 500*g for 10 min at 4° C. The supernatant was decanted and discarded. The pellets were re-suspended in 50 ml ice cold sterilized, ultrapure water and centrifuged at 500*g for 5 min at 4° C. This supernatant was also decanted and discarded. The pellets were re-suspended again in 50 ml ice cold sterilized, ultrapure water and centrifuged at 500*g for 5 min at 4° C. This supernatant was also decanted and discarded. The cells were then re-suspended in 20 ml ice cold, sterilized 1M sorbitol and centrifuged at 500*g for 5 min at 4° C. The supernatant was again decanted and discarded. The cells were then finally re-suspended in 250 µl 1M sorbitol.

Transformation of Competent *Pichia pastoris*

The prepared competent *Pichia* cells were transformed with the linearized plasmids, which were magnified in quantity by using *E. coli* as described above. To 100 µl competent *Pichia* cells, 10 µl linearized plasmid (2-4 µg) was added and the suspension was transferred to an electroporation cuvette with a gap of 2 mm. The cells were incubated on ice for 5 min and then electroporated at 1500V, 200Ω, 25 µF. To this mixture was added 1 ml ice cold 1M sorbitol and the mixture was incubated at 30° C. for 1 hour. The mixture was then centrifuged at 1000*g for 5 min at 21° C. and the supernatant decanted. The pellet was re-suspended in the remaining droplet of supernatant. Each colony was transferred to 5 ml YPD medium with 200 µg/ml zeocin with inoculation loop and incubated overnight at 28° C. and 180 rpm. For long term storage 1 ml of the culture was mixed with 0.5 ml 50% glycerol, shaken for 15 min at room temperature, and stored at −80° C.

Verification of Clone Expression and Activity

Tributyrin agar plate assay and SDS-PAGE analysis were run on all samples to verify that all tested clones showed activity towards tributyrin and that the expected lipase bands were observed. Activity of the cultures was measured by spectrophotometric activity assay, with p-NPD as the substrate. Protein content of the samples was analyzed by Bradford reagent following standard procedures. The results showed CR Lip1 clones had high level expression of the lipase. No activity was detected for any of the CR Lip5 clones, while moderate activity was measured for several CR Lip3 and CR Lip4 clones. Activities of CR Lip2 clones was typically very low. Shake flask expression needed to be performed to receive more constant growth conditions and therefore more reliable data.

Shake Flask Expression of AOX and GAP Constructs

For shake-flask expression of AOX-constructs, 25 ml BMGY medium in a 300 ml flask with baffles was inoculated using the glycerol stock. This preculture was incubated at 28° C. at 110 rpm for 24 hours. The cells were harvested by centrifugation (3000*g, 5 min, room temperature), re-suspended in 50 ml BMMY medium and filled into a 1000 ml flask with baffles and foam plug. For expression, the culture was incubated at 28° C. and 110 rpm for 96 hours. To maintain induction 250 µl methanol were added once a day. After 96 hours, the culture was centrifuged (3000*g, 5 min, 4° C.) and the supernatant transferred to a separate tube, which was stored at −20° C.

For shake-flask expression of GAP-constructs, 25 ml YPD medium in a 300 ml flask with baffles was inoculated using the glycerol stock. This preculture was incubated at 28° C. at 110 rpm overnight. The cells were harvested by centrifugation (3000*g, 5 min, room temperature), re-suspended in 100 ml YPD medium and filled into a 1000 ml flask with baffles and foam plug. For expression, the culture was incubated at 28° C. and 110 rpm for 96 hours. After 96 hours, the culture was centrifuged (5000*g, 10 min, 4° C.) and the supernatant transferred to a separate tube, which was stored at −20° C.

Spectrophotometric Activity Assay

Activity of the culture supernatants was measured by the spectrophotometric activity assay described above. As substrate, p-NPD (p-nitrophenyl decanoate) was used.

Protein content of the samples was analyzed by Bradford reagent following standard procedures. The specific activity of the samples in U/mg total protein was compared to the activities of 4 other commercial lipases from *Alcaligness* sp. (Al-1, Al-2, Al-3 and Al-4) and the commercial CRL preparation L11. The results are shown in Table 3.

TABLE 3

Activity numbers and protein content of *Pichia pastoris* shake flask expressions.

| System | Clone | Vol. activity (U/ml cell culture) p-NPD | Total protein content (mg/ml culture supernatant) | Specific activity (U/mg total protein in culture supernatant) p-NPD |
|---|---|---|---|---|
| AOX | 1.1 | 132.8 | 0.097 | 1362.4 |
|  | 1.4 | 0.5 | 0.085 | 5.9 |
|  | 2.2 | 0.1 | 0.087 | 1.3 |
|  | 3.3 | 5.9 | 0.081 | 72.2 |
|  | 3.4 | 5.2 | 0.079 | 65.9 |
|  | 4.1 | 16.5 | 0.094 | 175.5 |
|  | 4.2 | 18.5 | 0.097 | 190.2 |
| GAP | 1.3 | 80.9 | 0.071 | 1136.2 |
|  | 1.5 | 97.6 | 0.091 | 1070.1 |
|  | 2.2 | 0.5 | 0.092 | 5.4 |
|  | 3.2 | 5.9 | 0.107 | 54.5 |
|  | 4.4 | 9.4 | 0.121 | 77.4 |
|  | 4.5 | 10.6 | 0.098 | 107.9 |
|  | 5.1 | 0.0 | 0.127 | 0.0 |
| other | Al-1 |  |  | 717.0 |
|  | Al-2 |  |  | 83.8 |
|  | Al-3 |  |  | 142.5 |
|  | Al-4 |  |  | 63.0 |

Example 2—Comparison of Expression Levels in *P. pastoris* and *E. coli*

For comparison, expression of lipase isoforms in *Escherichia coli* was also performed. The genetic constructs were ordered as synthetic DNA from DNA2.0 and cloned in expression vectors harboring the neomycin resistance gene; the gene of interest is induced by L-arabinose via the pBAD promoter. The results are shown in Table 4.

TABLE 4

Comparison of achieved expression levels of *P. pastoris* and *E. coli*

| Isoform | Organism | System | Expression conditions | U/ml cell culture |
|---|---|---|---|---|
| CR Lip3 | *P. pastoris* | AOX | shake flask, 4 days | 5.8 (p-NPD) |
| CR Lip3 | *P. pastoris* | GAP | shake flask, 4 days | 5.9 (p-NPD) |
| CR Lip3 | *E. coli* | BAD | shake flask, 1 day | ~0.8 (p-NPD) |
| CR Lip4 | *E. coli* | BAD | shake flask, 1 day | ~15 (p-NPD) |
| CR Lip4 | *P. pastoris* | AOX | shake flask, 4 days | ~18 (p-NPD) |
| CR Lip4 | *P. pastoris* | GAP | shake flask, 4 days | ~10.6 (p-NPD) |
| CR Lip1 | *P. pastoris* | AOX | shake flask, 4 days | 130 (p-NPD) |
| CR Lip1 | *P. pastoris* | GAP | shake flask, 4 days | 97.6 (p-NPD) |
| CR Lip1 | *E. coli* | BAD | shake flask, 1 day | ~0.09 (p-NPD) |
| CR Lip2 | *P. pastoris* | AOX | shake flask, 4 days | 0.1 (p-NPD) |
| CR Lip2 | *P. pastoris* | GAP | shake flask, 4 days | 0.5 (p-NPD) |
| CR Lip2 | *E. coli* | BAD | shake flask, 1 day | ~0.05 (p-NPD) |

Example 3—*Candida rugosa* Lipase Hydrolyzation Experiments

To test the *Candida rugosa* lipase isoforms prepared according to Example 1 on the hydrolysis of fish oil, reactions at 35° C. were set up in pH-stat equipment in 40 ml scale without titration. The commercially available *Candida rugosa* lipase AY-30 from Amano (referred to as CRL11) was used as a comparative lipase. Due to the poor activity of CR Lip 2 and CR Lip5, only CR Lip1, CR Lip3 and CR Lip4 were used. The fish oil concentration was 50% (v/v). For CR Lip1 and CR Lip4, 8.6 U (based on p-NPD activity) per g fish oil were used corresponding to 0.1% (w/w) E/S for the commercial lipase. As buffer, 50 mM KPi pH 7.5 was used. Because of the low enzyme amount, the enzyme concentration for CR Lip3 was limited to 6.8 U per g fish oil and for CR Lip2 to 0.9 U (corresponding to 0.01% (w/w) E/S for the commercial lipase).

When possible, the fish oil was stirred at 2000 rpm with the buffer for approximately half an hour in the pH-stat before adding the enzyme while the pH was monitored. After starting the reaction by adding the enzyme, 2 ml samples were taken at different points in time, at 0 hours, 1 hour, 4 hours, 18 hours and 24 hours. These samples were analyzed with regard to the concentration of free fatty acids (FFA) and the EPA and DHA concentrations. To get all the free fatty acids into the oil layer, the emulsion was acidified with 3 M HCl, mixed well and centrifuged to separate the layers. If necessary, the samples were liquefied by heating up in an oven at 60° C. for some minutes.

Results of the hydrolyzation are shown in Tables 5 and 6, and illustrate the conversion and selectivities of the reactions. For the sake of comparison, extents of conversion are used to compare the selectivity of the commercial comparative example CRL11 sample to the CR Lip1, CR Lip3 and CR Lip4 samples since it is expected that, as the reaction runs to 100% conversion, all selectivity will be lost by all enzymes. It is useful, therefore, to use the extent of conversion as the milestone for comparison rather than time of reaction. It is expected that the time of reaction will vary for different enzymes isoforms and since time of reaction can be optimized by many different conditions it is recorded to make sure that reasonably times of reactions are observed, however, it is not used as a milestone for comparison.

TABLE 5

Effect of *Candida rugosa* lipase on EPA in FFA

| Sample | Oil (mg/mL)[1] | % Total FFA loss | EPA in oil (mg/mL) | % EPA loss[2] | % EPA loss in FFA[3] |
|---|---|---|---|---|---|
| CRL11 | 0.344 | −0.3 | 0.00004 | −0.01 | −3.63 |
|  | 0.356 | −11.2 | 0.00149 | −0.42 | −3.74 |
|  | 0.337 | −18.6 | 0.00284 | −0.84 | −4.54 |
|  | 0.348 | −29.5 | 0.00492 | −1.41 | −4.79 |
|  | 0.278 | −31.6 | 0.00447 | −1.61 | −5.09 |
| CR Lip1 | 0.329 | −0.2 | 0.00002 | −0.01 | −2.93 |
|  | 0.385 | −6.1 | 0.00070 | −0.18 | −2.97 |
|  | 0.361 | −11.4 | 0.00113 | −0.31 | −2.74 |
|  | 0.342 | −20.1 | 0.00288 | −0.84 | −4.19 |
|  | 0.37 | −21.8 | 0.00363 | −0.98 | −4.51 |
| CR Lip3 | 0.356 | −0.2 | 0.00005 | −0.01 | −3.4 |
|  | 0.296 | −6.8 | 0.000 | −0.04 | −0.86 |
|  | 0.371 | −12.1 | 0.00031 | −0.09 | −0.91 |
|  | 0.411 | −22.7 | 0.00111 | −0.27 | −1.39 |
|  | 0.5 | −24.7 | 0.00103 | −0.34 | −1.69 |
| CR Lip4 | 0.394 | −0.4 | 0.00002 | −0.01 | −2.88 |
|  | 0.454 | −5.1 | 0.00136 | −0.46 | −6.76 |
|  | 0.34 | −10.0 | 0.00275 | −0.74 | −6.15 |
|  | 0.411 | −19.4 | 0.00811 | −1.97 | −8.71 |
|  | 0.305 | −20.0 | 0.01053 | −2.11 | −8.53 |

[1]Oil = concentration of EPA and DHA measured after diluting with THF
[2]% EPA loss is % of free fatty acid EPA = (EPA in oil/oil) × 100
[3]% EPA loss in FFA is % of free EPA related to the total loss of FFA = (% EPA loss/% Total FFA loss) × 100

TABLE 6

Effect of *Candida rugosa* lipase on DHA in FFA

| Sample | Oil (mg/mL)[1] | % Total FFA loss | DHA in oil (mg/mL) | % DHA loss[2] | % DHA loss in FFA[3] |
|---|---|---|---|---|---|
| CRL11 | 0.344 | −0.3 | 0.00003 | −0.1 | −2.87 |
|  | 0.356 | −11.2 | 0.00011 | −0.03 | −0.26 |
|  | 0.337 | −18.6 | 0.00018 | −0.05 | −0.28 |
|  | 0.34 | −29.5 | 0.00034 | −0.10 | −0.33 |
|  | 0.278 | −31.6 | 0.00030 | −0.11 | −0.34 |
| CR Lip1 | 0.326 | −0.2 | 0.00002 | −0.01 | −2.77 |
|  | 0.385 | −6.1 | 0.00003 | −0.01 | −0.13 |
|  | 0.361 | −11.4 | 0.00004 | −0.01 | −0.09 |
|  | 0.342 | −20.1 | 0.00009 | −0.03 | −0.13 |
|  | 0.37 | −21.8 | 0.00009 | −0.03 | −0.12 |
| CR Lip3 | 0.394 | −0.4 | 0.00002 | −0.01 | −1.50 |
|  | 0.454 | −5.1 | 0.00004 | −0.01 | −0.15 |
|  | 0.34 | −10.0 | 0.00003 | −0.01 | −0.10 |
|  | 0.411 | −19.4 | 0.00011 | −0.03 | −0.13 |
|  | 0.305 | −20.0 | 0.00008 | −0.03 | −0.13 |
| CR Lip4 | 0.356 | −0.2 | 0.00002 | −0.01 | −2.87 |
|  | 0.296 | −6.8 | 0.00003 | −0.01 | −0.13 |
|  | 0.371 | −12.1 | 0.00004 | −0.01 | −0.09 |
|  | 0.411 | −22.7 | 0.00014 | −0.03 | −0.15 |
|  | 0.5 | −24.7 | 0.00016 | −0.03 | −0.13 |

[1]Oil = concentration of EPA and DHA measured after diluting with THF
[2]% DHA loss is % of free fatty acid DHA = (DHA in oil/oil) × 100
[3]% DHA loss in FFA is % of free DHA related to the total loss of FFA = (% DHA loss/% Total FFA loss) × 100

Example 4—*Geotrichum candidum* Lipase Hydrolyzation Experiments

In these examples, the lipase gene-encoding polynucleotide sequences from *Geotrichum candidum* were identified and expressed in *Pichia pastoris* as described in Example 1 above. The commercially available *Candida rugosa* lipase AY-30 from Amano (referred to as CRL11) was used as a comparative lipase.

For each sample (GC Lip1, GC Lip 2 and CRL11), the following process was used: About 20 g fish oil, 3 mL of a 0.95 mg/mL lipase solution, and 12.0 mL of BES buffer (50 mM, pH 7.0) were placed in a 100 mL flask, and stirred at 37° C. at 360 rpm under $N_2$ gas. The reaction progress was monitored by monitoring the acid value by the method described above, Determination of free fatty acids. The reaction was stopped by heating to 85° C. for 10 minutes. The mixture was washed with 25 mL of brine and 25 mL of water, and the oil dried under vacuum (1 torr). The glycerides and fatty acids were separated as follows: 10 g of oil was added to 75 mL of hexane and 25 mL of ethyl acetate. The organic layer was then extracted twice with a solution 40 mL of 0.5M sodium hydroxide and 40 mL of ethanol. The upper organic layer was then washed with water; solvent was removed under reduced pressure and dried under high vacuum to give the glycerides. The lower alkaline layer was then acidified to pH 1 with 3M HCl, and extracted with 75 mL of hexane and 75 mL of chloroform, and the combined organics evaporated to give the fatty acid layers. The fatty acid profiles of the separated glyceride and fatty acids were determined by the EP2.4.29 method. Results are shown in Tables 7 and 8.

The experiment was repeated using GC Lip2 and an oil composition which contains about 22% EPA and 10% DHA. The results are shown in Tables 9 and 10.

TABLE 7

Effect of *Geotrichum candidum* lipase on EPA in FFA on 18:15 oil

| Sample | % FFA | EPA FFA in oil (mg/g) | % EPA loss in FFA |
|---|---|---|---|
| Starting oil | 0.1 | 0 | n/a |
| CRL11 | 26 | 48 | 5.4 |
| GC Lip1 | 14 | 53 | 5.6 |
| GC Lip1 | 14 | 54 | 6.1 |
| GC Lip2 | 27 | 28 | 3.0 |
| GC Lip2 | 25 | 31 | 3.3 |

TABLE 8

Effect of *Geotrichum candidum* lipase on DHA in FFA on 18:15 oil

| Sample | % FFA | DHA FFA in oil (mg/g) | % DHA loss in FFA |
|---|---|---|---|
| Starting oil | 0.1 | 0 | n/a |
| CRL11 | 26 | 15 | 1.6 |
| GC Lip1 | 14 | 8 | 0.9 |
| GC Lip1 | 14 | 11 | 1.1 |
| GC Lip2 | 27 | 11 | 1.2 |
| GC Lip2 | 25 | 14 | 1.6 |

TABLE 9

Effect of *Geotrichum candidum* lipase on EPA in FFA on 22:10 oil

| Sample | % FFA | EPA FFA in oil (mg/g) | % EPA loss in FFA |
|---|---|---|---|
| Starting oil | 0.1 | 0 | n/a |
| CRL11 | 24.1 | 56 | 5.8 |
| GC Lip2 | 17.3 | 24 | 2.8 |
| GC Lip2 | 21.7 | 28 | 2.9 |

TABLE 10

Effect of *Geotrichum candidum* lipase on DHA in FFA on 22:10 oil

| Sample | % FFA | DHA FFA in oil (mg/g) | % DHA loss in FFA |
|---|---|---|---|
| Starting oil | 0.1 | 0 | n/a |
| CRL11 | 24.1 | 10 | 1.0 |
| GC Lip2 | 17.3 | 8 | 0.9 |
| GC Lip2 | 21.7 | 8 | 0.9 |

What is claimed is:

1. A host cell transformed with a nucleic acid molecule comprising a polynucleotide sequence having at least 90% identity to SEQ ID NO:1, SEQ ID NO:2, or SEQ ID NO:3, wherein the polynucleotide sequence encodes a polypeptide that hydrolyzes an ester linkage of a triacylglycerol in an oil comprising at least one long-chain polyunsaturated fatty acid (LC-PUFA).

2. The host cell of claim 1 wherein the host cell is *Pichia pastoris*.

3. The host cell of claim 1 or claim 2, wherein the polynucleotide sequence has a 90% to 99% identity to SEQ ID NO:1, SEQ ID NO:2, or SEQ ID NO:3.

4. The host cell of claim 1, wherein the polynucleotide sequence encodes a lipase gene.

5. The host cell of claim 1, wherein the polynucleotide sequence encodes a *Candida rugosa* lipase 1 gene.

6. The host cell of claim 1, wherein the polynucleotide sequence encodes a *Candida rugosa* lipase 3 gene.

7. The host cell of claim 1, wherein the polynucleotide sequence encodes a *Geotrichum candidum* lipase 2 gene.

8. The host cell of claim 1, wherein the long-chain polyunsaturated fatty acid comprises eicosopentaenoic acid (EPA), docosahexaneoic acid (DHA), and combinations thereof.

9. The host cell of claim 1, wherein the oil is a crude or unrefined oil.

10. The host cell of claim 1, wherein the oil is a marine oil.

11. A method of using a host cell transformed with a nucleic acid molecule comprising a polynucleotide sequence having at least 90% identity to SEQ ID NO:1, SEQ ID NO:2, or SEQ ID NO:3, wherein the polynucleotide sequence encodes a polypeptide that hydrolyzes an ester linkage of a triacylglycerol in an oil comprising at least one long-chain polyunsaturated fatty acid.

12. The method of claim 11, wherein the host cell is *Pichia pastoris*.

13. The method of claim 11 or claim 12, wherein the polynucleotide sequence has a 90% to 99% identity to SEQ ID NO:1, SEQ ID NO:2, or SEQ ID NO:3.

14. The method of claim 11 wherein the polynucleotide sequence encodes a lipase gene.

15. The method of claim 11, wherein the polynucleotide sequence encodes a *Candida rugosa* lipase 1 gene.

16. The method of claim 11, wherein the polynucleotide sequence encodes a *Candida rugosa* lipase 3 gene.

17. The method of claim 11, wherein the polynucleotide sequence encodes a *Geotrichum candidum* lipase 2 gene.

18. The method of claim 11, wherein the long-chain polyunsaturated fatty acid comprises eicosopentaenoic acid (EPA), docosahexaneoic acid (DHA), and combinations thereof.

19. The method of claim 11, wherein the oil is a crude or unrefined oil.

20. The method of claim 11, wherein the oil is a marine oil.

21. The host cell of claim 1 or claim 2, wherein the polynucleotide sequence has at least 95% identity to SEQ ID NO:1, SEQ ID NO:2, or SEQ ID NO:3.

22. The host cell of claim 1 or claim 2, wherein the polynucleotide sequence has 100% identity to SEQ ID NO:1, SEQ ID NO:2, or SEQ ID NO:3.

* * * * *